United States Patent [19]

Mault

[11] Patent Number: 5,836,300
[45] Date of Patent: Nov. 17, 1998

[54] METABOLIC GAS EXCHANGE AND NONINVASIVE CARDIAC OUTPUT MONITOR

[76] Inventor: James R. Mault, 5804 Renee Dr., Durham, N.C. 27705

[21] Appl. No.: 814,677

[22] Filed: Mar. 11, 1997

Related U.S. Application Data

[60] Provisional application No. 60/018,082 May 22, 1996 and provisional application No. 60/013,152 Mar. 11, 1996.

[51] Int. Cl.$^6$ .................................................. A61M 16/00
[52] U.S. Cl. ...................... 128/204.23; 600/529; 600/532
[58] Field of Search ........................ 128/204.22, 204.23; 600/532, 529, 531, 538, 484

[56] References Cited

U.S. PATENT DOCUMENTS

| | | | |
|---|---|---|---|
| 2,630,798 | 3/1953 | White et al. | 128/2.07 |
| 2,838,399 | 6/1958 | Vogel, Jr. | 99/48 |
| 2,920,012 | 1/1960 | Sanders et al. | 167/51.5 |
| 3,213,684 | 10/1965 | Seaton et al. | 73/190 |
| 3,250,270 | 5/1966 | Bloom | 128/2.07 |
| 3,306,283 | 2/1967 | Arp | 128/719 |
| 3,523,529 | 8/1970 | Kissen | 128/2.07 |
| 3,527,205 | 9/1970 | Jones | 128/719 |
| 3,681,197 | 8/1972 | Smith | 195/63 |
| 3,726,270 | 4/1973 | Griffis et al. | 128/2.08 |
| 3,797,480 | 3/1974 | Williams | 128/2.08 |
| 3,799,149 | 3/1974 | Rummel et al. | 128/2.07 |
| 3,814,091 | 6/1974 | Henkin | 128/188 |
| 3,834,375 | 9/1974 | Sanctuary et al. | 128/2.07 |
| 3,895,630 | 7/1975 | Bachman | 128/2.07 |
| 3,938,551 | 2/1976 | Henkin | 137/613 |

(List continued on next page.)

OTHER PUBLICATIONS

Medical Progress through Technology, vol. 9, No. 1, 1982, Berlin (D) pp. 27–32, R. Salminen et al. "Computerized Breath–by–Breath Analysis of Respiratory Variables During Exercise".

British Journal of Anaesthesia, vol. 49, 1977, London (GB) pp. 575–587, J.A. Bushman et al. "Closed Circuit Anaesthesia".

IEEE Transactions on Biomedical Engineering, vol. 35, No. 9, Sep. 1988, pp. 653–659, Capek et al., "Noninvasive Measurement of Cardiac Output Using Partial $CO_2$ Rebreathing".

Clinics in Chest Medicine [Review], vol. 10, 1989, pp. 255–264, Heigenhauser et al., "Measurement of Cardiac Output by Carbon Dioxide Rebreathing Methods".

*Primary Examiner*—Mickey Yu
*Assistant Examiner*—V. Srivastava
*Attorney, Agent, or Firm*—Gifford, Krass, Groh, Sprinkle, Patmore, Anderson & Citkowski, PC

[57] ABSTRACT

A respiratory gas analyzer for measuring the metabolic activity and the cardiac output of a subject includes a bi-directional flow meter and a capnometer sensor interconnected by conduits and valving between a mouthpiece and a source of respiratory gasses which may be a controlled source or the atmosphere. A pass-through carbon dioxide scrubber may be plugged into the conduits and the valving controlled so that upon inhalation by the subject gasses are passed through the flow meter to the mouthpiece and upon exhalation the exhaled gasses are passed first through the scrubber and then through the flow meter in a direction opposite to the inhaled gasses. A computer connected to receive the signals from the flow meter and the capnometer can then calculate the subject's metabolic activity. When the valving is shifted a portion of the exhaled gasses are stored in the conduit so that upon inhalation the subject inhales a substantial portion of rebreathed gasses. The computer can then calculate the patient's cardiac output as a function of the changes in total carbon dioxide content of the exhaled gas before and after the valve is shifted from a direct input to a rebreathed position and the difference in end-tidal carbon dioxide between these two positions. The carbon dioxide scrubber may be removed from the circuitry during calculation of cardiac output to conserve the scrubber life.

5 Claims, 3 Drawing Sheets

U.S. PATENT DOCUMENTS

| | | | |
|---|---|---|---|
| 4,051,847 | 10/1977 | Henkin | 128/145.6 |
| 4,186,735 | 2/1980 | Henneman et al. | 128/201.25 |
| 4,188,946 | 2/1980 | Watson et al. | 128/204.22 |
| 4,200,094 | 4/1980 | Gedeon et al. | 128/201.13 |
| 4,211,239 | 7/1980 | Raemer et al. | 128/716 |
| 4,221,224 | 9/1980 | Clark | 128/718 |
| 4,341,867 | 7/1982 | Johansen | 435/189 |
| 4,359,057 | 11/1982 | Manzella | 128/718 |
| 4,368,740 | 1/1983 | Binder | 128/718 |
| 4,386,604 | 6/1983 | Hershey | 128/718 |
| 4,444,201 | 4/1984 | Itoh | 128/716 |
| 4,572,208 | 2/1986 | Cutler et al. | 128/718 |
| 4,598,700 | 7/1986 | Tamm | 128/671 |
| 4,608,995 | 9/1986 | Linnarsson et al. | 128/719 |
| 4,619,269 | 10/1986 | Cutler et al. | 128/719 |
| 4,753,245 | 6/1988 | Gedeon | 128/718 |
| 4,756,670 | 7/1988 | Arai | 417/43 |
| 4,917,108 | 4/1990 | Mault | 128/719 |
| 5,022,406 | 6/1991 | Tomlinson | 128/719 |
| 5,038,792 | 8/1991 | Mault | 128/718 |
| 5,060,656 | 10/1991 | Howard | 128/719 |
| 5,095,913 | 3/1992 | Yelderman et al. | 128/719 |
| 5,178,155 | 1/1993 | Mault | 128/718 |
| 5,179,958 | 1/1993 | Mault | 128/719 |
| 5,293,875 | 3/1994 | Stone | 128/719 |
| 5,402,796 | 4/1995 | Parker et al. | 128/719 |
| 5,632,281 | 5/1997 | Rayburn | 128/719 |

METABOLIC GAS EXCHANGE AND NONINVASIVE CARDIAC OUTPUT MONITOR

CROSS REFERENCE TO RELATED APPLICATIONS

This application claims the benefit of U.S. Provisional application Ser. No. 60/013,152, filed Mar. 11, 1996 and U.S. Provisional application Ser. No. 60/018,082 filed May 22, 1996.

FIELD OF THE INVENTION

This invention relates to a respiratory gas analyzer employing a flow sensor and a capnometer which may be interconnected in a first configuration to measure metabolic activity of a patient or in a second configuration to measure the cardiac output of the patient.

BACKGROUND OF THE INVENTION

My U.S. Pat. No. 5,179,958 and related patents including 5,038,792 and 4,917,708 disclose respiratory calorimeters connected to a mouthpiece which measure the volume of gas inhaled by a patient over a period of time and pass the exhaled gasses through a carbon dioxide scrubber and then a flow meter. Broadly, the integrated flow differences between the inhalations and the carbon dioxide scrubbed exhalations are a measure of the patient's oxygen consumption and thus the patient's metabolic activity. These devices may incorporate a capnometer to measure the carbon dioxide concentration of the exhaled air. A computer receiving signals from the flow meter and the capnometer may calculate, in addition to the oxygen consumption of the patient, the Respiratory Quotient and the Resting Energy Expenditure of the patient as calculated from the Weir equation.

The cardiac output of a patient, that is the volume of blood ejected from the heart per unit time, is another important measured parameter in hospitalized patients. Currently, cardiac output is routinely measured by invasive techniques including thermal dilution using an indwelling pulmonary artery catheter. This technique has several disadvantages including the morbidity and mortality of placing an invasive intracardiac catheter, the infectious disease risks, significant expense and the fact that it provides an intermittent rather than a continuous measurement. A noninvasive, reusable, continuous cardiac output measurement device would substantially improve patient care and reduce hospital costs.

The partial rebreathing technique is a known method for cardiac output measurement. As described in Capek and Roy, "The Noninvasive Measurement of Cardiac Output Using Partial $CO_2$ Rebreathing", *IEEE Transactions on Biomedical Engineering*, Vol. 35, No. 9, Sep. 1988, pp. 653–659, the method utilizes well known Fick procedures, substituting carbon dioxide for oxygen, and employing a sufficiently short measurement period such that venous carbon dioxide levels and cardiac output can be assumed to remain substantially constant during the measurement. In its original form, the Fick method of measuring cardiac output requires blood gas values for arterial and mixed venous blood as follows:

$$C.O. = VO_2/CaO_2 - CvO_2$$

where C.O. is cardiac output, $VO_2$ is oxygen consumption, $CaO_2$ is the arterial oxygen content and $CvO_2$ is the venous oxygen content. By substituting carbon dioxide for oxygen in the Fick equation, the partial rebreathing method allows computation of cardiac output without invasive blood gas measurements as follows:

$$C.O. = VCO_2/CaCO_2 - CvCO_2$$

The partial rebreathing technique uses the change in $CO_2$ production ($VCO_2$) and end-tidal $CO_2$ in response to a brief change in ventilation. The change in $CO_2$ production divided by the change in $CO_2$ content of arterial blood ($CaCO_2$), as estimated from end-tidal $CO_2$, equals pulmonary capillary blood flow as follows:

$$C.O. = \Delta VCO_2/\Delta etCO_2$$

Clinical studies have verified the accuracy of this partial rebreathing method relative to more conventional invasive techniques. Despite the advantages of the partial rebreathing technique it has not achieved extensive usage.

I have discovered that minor modifications of my respiratory calorimeter will enable it to practice cardiac output measurement using the partial carbon dioxide rebreathing technique as well as making the metabolic related measurements described in my patent.

SUMMARY OF THE INVENTION

The present invention is accordingly directed toward a respiratory gas analyzer capable of measuring either the metabolic activity or the cardiac output of a subject. The configuration of the preferred embodiment of the analyzer substantially resembles the indirect calorimeter disclosed in my previous patents in that it incorporates a bi-directional flow meter, a capnometer and a carbon dioxide scrubber. Conduits connect the flow meter between a source of respiratory gasses, which is typically atmospheric air, and a mouthpiece, so that the flow meter measures the gas volume during inhalation. During exhalation the gas is passed through a capnometer to the carbon dioxide scrubber and the output of the scrubber is fed back through the flow meter to the atmosphere. In this configuration the computer connected to receive the electrical outputs of the flow meter and capnometer calculates the patient's oxygen consumption either alone or along with one or more of the derivative measurements of Respiratory Quotient and Respiratory Energy Expenditure.

In order to perform measurements of patient's cardiac output using partial $CO_2$ rebreathing the system is convertible into the configuration in which the exhaled breath is not passed through the carbon dioxide scrubber but is rather passed directly to the flow meter or into an interior volume within the analyzer that connects to the flow meter but allows the accumulation of a fraction of an exhalation which is then mixed with additional air passing through the flow meter on the next inhalation to increase the carbon dioxide content of that subsequent inhalation. The analyzer may be formed so that the carbon dioxide scrubber is completely removable for purposes of taking cardiac output measurements, or, alternatively, the scrubber may be maintained in position on the analyzer with the flow passages altered so that the exhaled air is not passed through the scrubber.

The analyzer further includes valving connected to the circuitry to shift the circuitry between two alternative configurations. In the first configuration exhaled gasses are passed through the capnometer and then directly to the flow meter. Upon the subsequent inhalation fresh respiratory gasses are drawn through the flow meter. In the second alternative configuration, after the valve is shifted, the exhaled gasses are passed through the capnometer and then fed into a conduit connecting to the flow meter. The conduit volume thus acts as a dead space. When the subject then inhales a substantial portion of the inhaled gasses constitutes rebreathed gasses from the conduit dead space having a high carbon dioxide content. Preferably from 20% to 70% of the inhaled air constitutes rebreathed air, with the balance being made up of air drawn in through the flow meter with the inhalation.

The metabolic measurements are made with the scrubber connected in operative configuration so that exhaled air passes through the carbon dioxide scrubber and then the flow meter. A computer connected to the flow meter integrates the inhaled and exhaled flow signals. Their difference is a function of the subject's metabolic rate. To use the device to calculate cardiac output, the scrubber is either removed or its input is blocked and the computer receives signals from the flow meter and the capnometer while the subject breathes while the valve is in the first configuration in which the exhaled gas is passed through the capnometer and then directly out through the flow meter. The computer integrates the capnometer measurement over the flow volume to determine the carbon dioxide content of the exhalations and also determines the carbon dioxide content of an exhalation at the end of the breath; i.e. the end-tidal carbon dioxide measurement. The valve is then shifted to bring the circuitry into the alternate configuration in which the exhaled breath is introduced into the dead space volume within the circuitry so that only a proportion of each exhaled breath passes out through the flow sensor. Each inhaled breath includes a proportion of rebreathed air having an increased carbon dioxide content. Measurement is made for about thirty seconds during which time the computer again measures the end-tidal carbon dioxide. This measurement is used with the measurements made while the valve was in its first configuration to calculate cardiac output.

Alternatively, the volume of the flow chamber containing rebreathed air is made adjustable and/or computer controlled so as to adjust the dead space to the breath volume of the user.

Other objects, advantages and applications of the present invention will be made apparent from the following detailed description of the preferred embodiments.

DETAILED DESCRIPTION OF THE INVENTION

Figure 1:
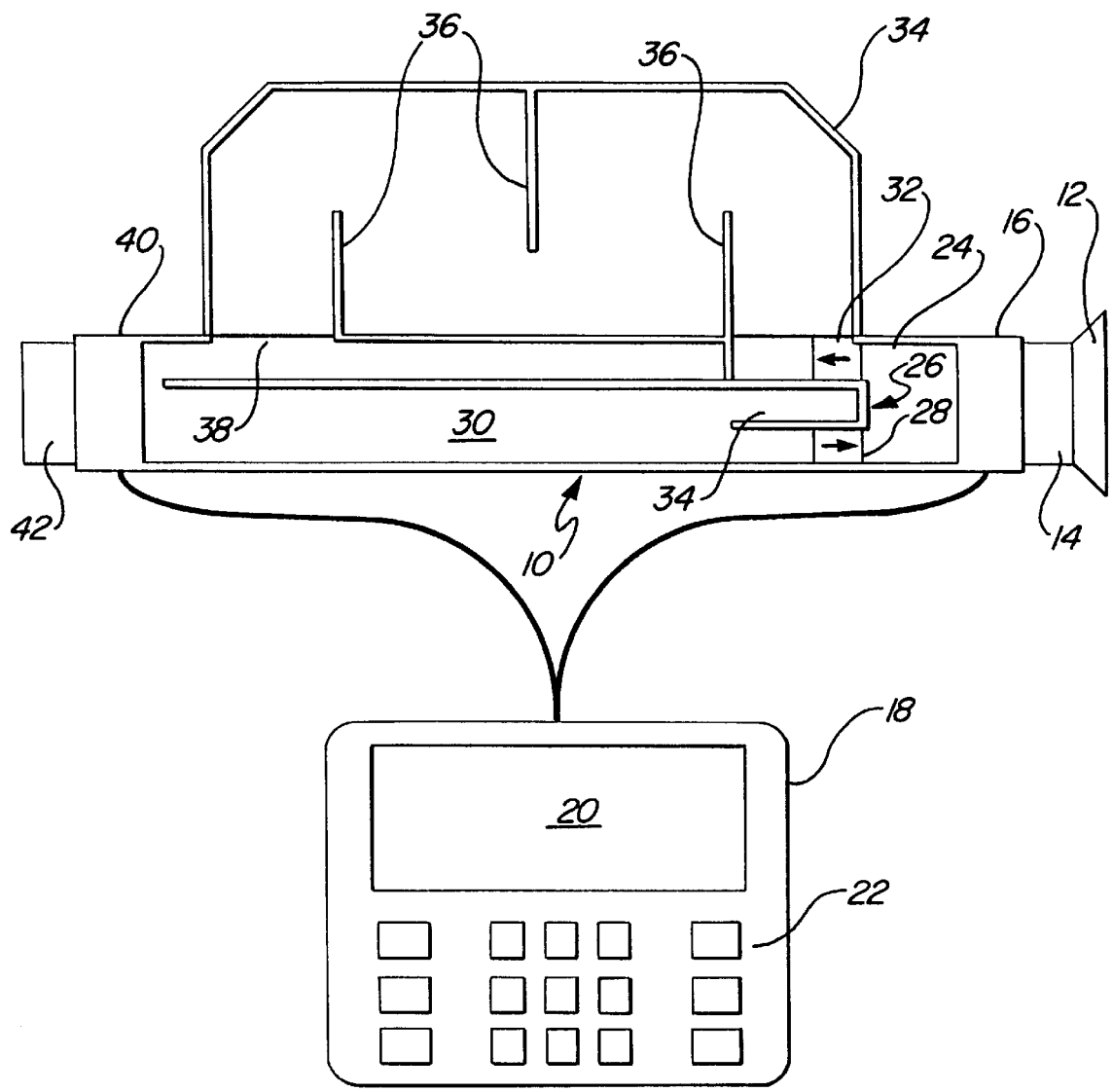
FIG. 1 is a schematic diagram illustrating a preferred embodiment of my invention in the configuration which measures metabolic activity.

The preferred embodiment of the invention, as illustrated in FIG. 1, and generally indicated at 10 is in a configuration in which it may be used to measure a patient's metabolic activity. The analyzer employs a mouthpiece 12 adapted to engage the inner surfaces of the user's mouth, so as to form the sole passage for flowing respiratory gasses into and out of the mouth. A nose clamp of conventional construction (not shown) may be employed in connection with the mouthpiece 12 to assure that all respiratory gas passes through the mouthpiece. In alternative configurations, a mask that engages the nose as well as the mouth might be employed or an endotracheal tube could be used.

The mouthpiece 12 connects through a short passage 14 to a capnometer sensor 16. The capnometer 16 generates an electrical signal which is a function of the instantaneous carbon dioxide concentration of gas passing through the mouthpiece 12. The capnometer may be of a conventional type such as those described in U.S. Pat. Nos. 4,859,858; 4,859,859; 4,914,720 or 4,958,075. The capnometer provides an electrical output signal to a computation unit 18 incorporating a suitably programmed microprocessor (not shown), a display 20, and a keypad 22.

The capnometer is connected by a short passage 24 to a two position, three-way valve, generally indicated at 26. The valve has a single input flow channel from a one-way valve 28 which connects to a gas flow conduit 30. The valve has a first position, illustrated in FIG. 1, in which output is provided to a second one-way valve 32 connecting to the input of a carbon dioxide scrubber 34. In its second position, schematically illustrated in FIG. 3, the valve is shifted so as to block gas flow to the valve 32 and thus the scrubber and to direct flow to an air passage 34 which connects with the gas conduit volume 30.

The carbon dioxide scrubber 34 is a container having a central gas passageway filled with a carbon dioxide absorbent material such as sodium hydroxide or calcium hydroxide. Such absorbent materials may include sodium hydroxide and/or calcium hydroxide mixed with silica in a form known as "Soda Lime™." Another absorbent material which may be used is "Baralyme™" which comprises a mixture of barium hydroxide and calcium hydroxide. The carbon dioxide scrubber has internal baffles 36 which provide a labyrinth flow of gasses.

The output 38 of the scrubber is located adjacent to a bi-directional volume flow sensor 40 which is positioned at the end of the volume 30 opposite to the valve 26. The flow sensor is preferably of the pressure differential type such as manufactured by Medical Graphics Corporation of St. Paul, Minn. under the trademark "Medgraphics" of the general type illustrated in U.S. Pat. No. 5,038,773. Alternatively other types of flow transducers such as pneumatics or spirameters might be employed. The other end of the flow sensor is connected to a source and sink for respiratory gasses through a line 42. The source and sink is typically the atmosphere but may alternatively be a suitable form of positive pressure ventilator. The electrical output of the bi-directional volume flow sensor is connected to the computation unit 18.

With the valve 26 in the first position schematically illustrated in FIG. 1, the system operates in the same manner as the unit described in my U.S. Pat. No. 5,179,958 to calculate various respiratory parameters of the patient such as oxygen consumption per unit time, the Respiratory Quotient (RQ) which equals $VCO_2$ divided by $VO_2$, and the Resting Energy Expenditure (REE) preferably calculated from the Weir equation.

In this mode of operation, assuming that room air is being inhaled, an inhalation by the subject on the mouthpiece 12 draws room air in through the intake 42 through the flow meter 40, generating an electrical signal to the computation unit 18. The inhaled air then passes through the volume 30 and through the one-way valve 28, to the passage 24 leading to the capnometer sensor 16. The sensor 16 generates an electrical signal which is provided to the computation unit 18. The inhaled air then passes through the passage 14 to the patient via the mouthpiece 12. When the patient exhales the expired gasses pass through the capnometer 16 in the reverse direction and then through the one-way valve 32 to the input of the carbon dioxide scrubber 34. The scrubber absorbs the carbon dioxide in the exhaled breath and provides its output into the volume 30 immediately adjacent the bi-directional volume flow sensor 40 in a direction opposite to the inhaled gas.

The volume of exhaled air passing through the flow sensor 40 will be lower than the volume of inhaled air because of the absorption of the carbon dioxide by the scrubber 34. This difference in volume is a function of the oxygen absorbed from the inhaled air by the patient's lungs. The computation unit 18 converts the signals from the capnometer 16 and the flow sensor 40 into digital form if the signals are in analog form, as employed in the preferred embodiment of the invention. The computation unit 18 otherwise operates in the manner disclosed in my U.S. Pat. 4,917,718 to integrate signals representing the difference between the inhaled and exhaled volume for the period of the test and multiply them by a constant to arrive at a display of kilocalories per unit time. The Resting Energy Expenditure (REE) and the Respiratory Quotient (RQ) are similarly calculated. The keyboard 22 associated with the computation unit 18 allows storage and display of various factors in the same manner as the systems of my previous patent.

The unit may incorporate an artificial nose and/or a bacterial filter as described in my previous patents or may incorporate a temperature sensor which provides a signal to the computation unit 18 to adjust the measurements as a function of the breath and external air temperature.

In order to use the analyzer to noninvasively measure the patient's cardiac output, the connections between scrubber 34 and the main body of the unit are blocked. The scrubber may be physically removed from the main unit or may continue to be supported on the main unit with appropriate valving (not shown) shifted to block off the scrubber so it is inoperative during the measurement.

Figure 2:
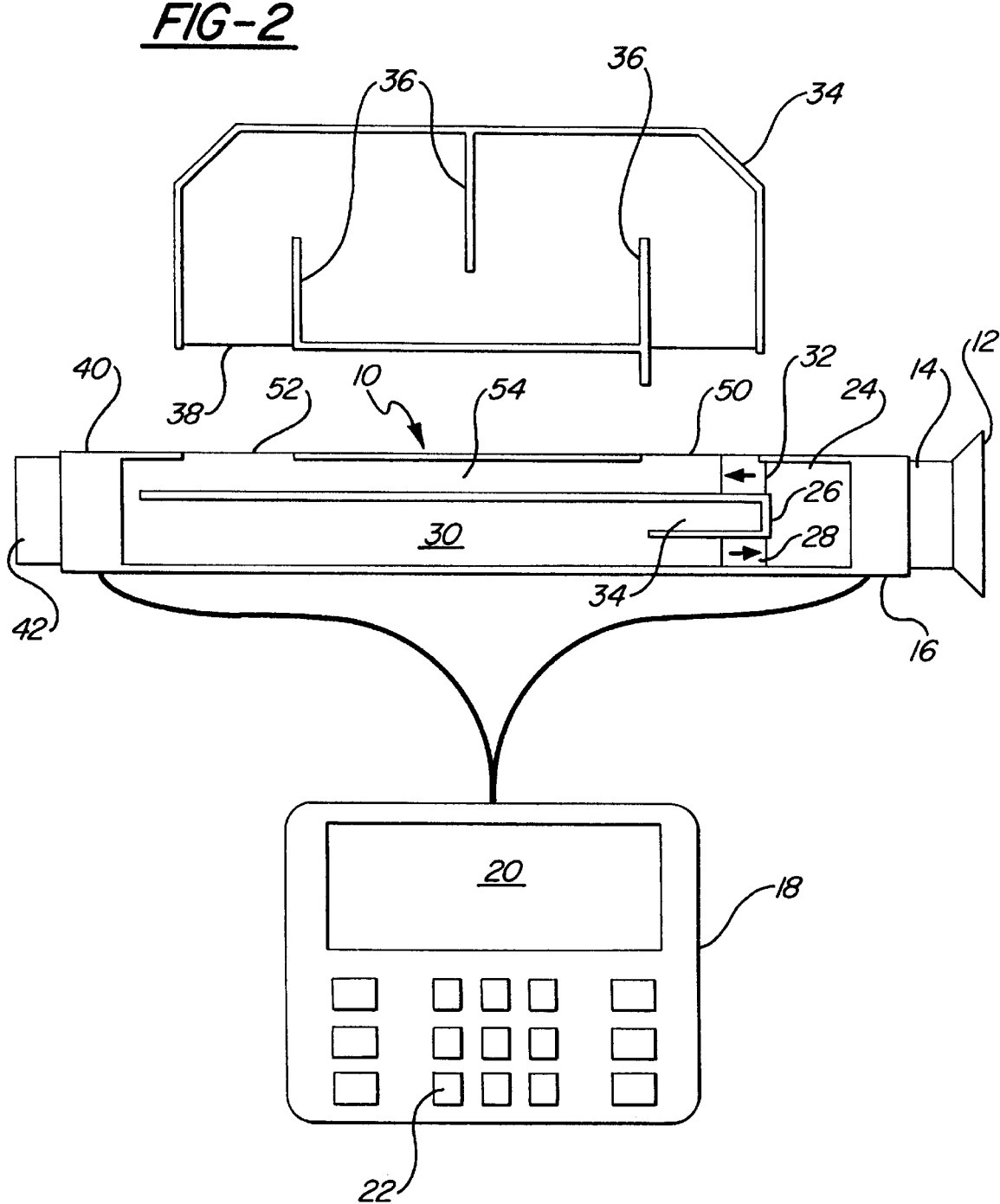
FIG. 2 is a schematic diagram of the system of FIG. 1 in a configuration for making the first measurements required to determine a patient's cardiac output.

FIG. 2 illustrates the unit with the scrubber 34 physically detached and with wall sections 50 and 52 blocking off the ports in the main body to which the input and output connections of the scrubber 34 connect. This creates a relatively narrow, low volume passage 54 connecting the output of the one way valve 32 to the area adjacent the flow meter 40.

In this position, when the patient inhales air or respiratory gasses are drawn in through the inlet 42, passed through the bi-directional sensor 40, passed through the volume 30 and the one way valve 28, through the capnometer 16 to the mouthpiece 12. When the patient exhales, gasses are passed from the mouthpiece 12, through the passage 14, through the capnometer 16, through the one way valve 32 and the passage 54 and out the bi-directional sensor 40.

Figure 3:
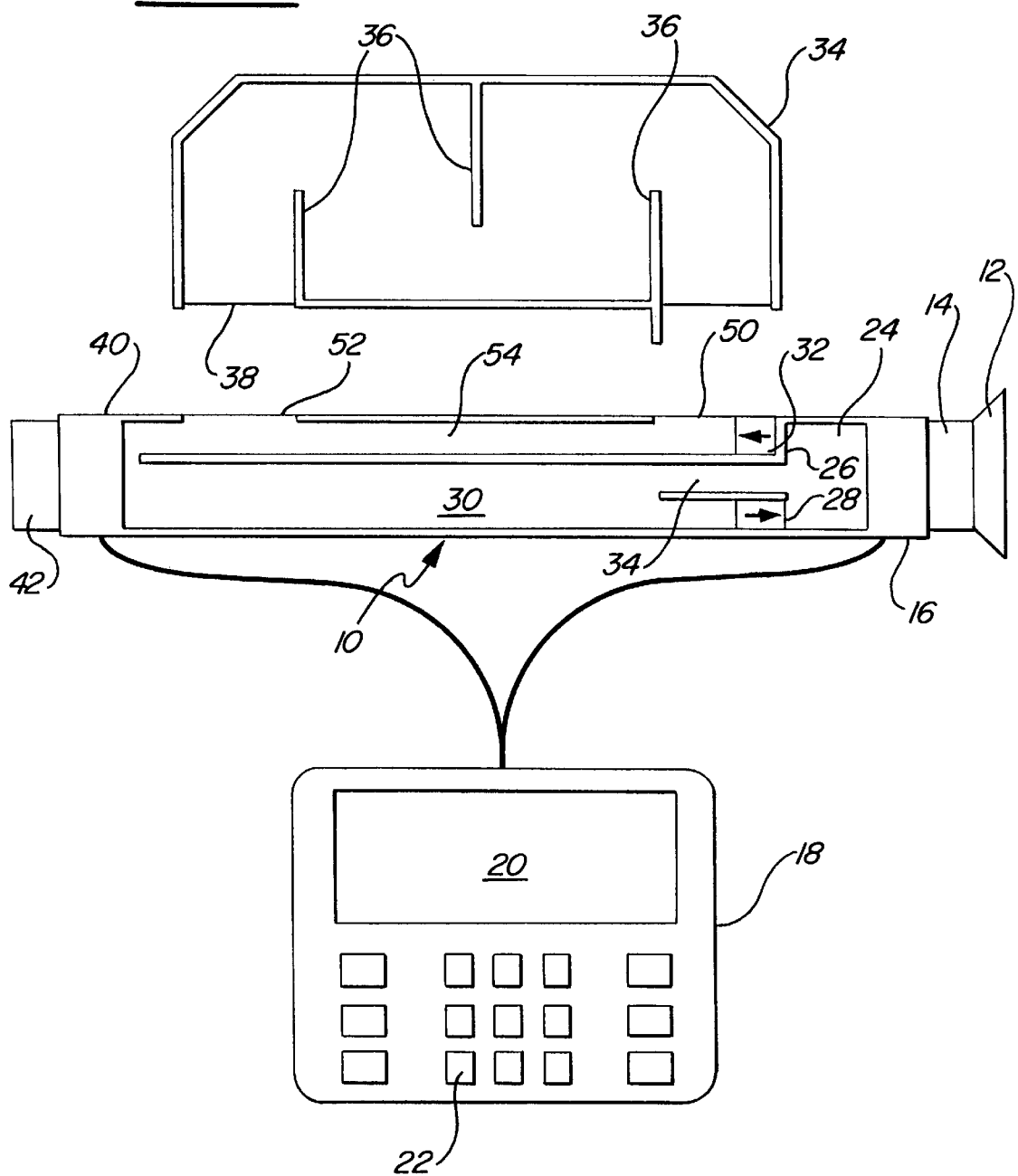
FIG. 3 is a schematic diagram of the system of FIG. 1 in a configuration for making the second measurement required to determine cardiac output.

The computation unit 18 may control the two position valve 26 and move it to a second position, illustrated schematically in FIG. 3, in which the flow passage to the one-way valve 32 is blocked and the passage 34 is open to the flow volume 24 adjacent the capnometer 16. The shifted valve prevents exhaled gasses from entering the passage 56 and instead returns the exhaled gasses back in the direction of the flow sensor 40 through the conduit volume 30. This creates a temporary increase in dead space that causes rebreathing of carbon dioxide enriched air from the volume 30 when the patient inhales to create changes in the carbon dioxide content of the exhalation ($VCO_2$) and in the end-tidal carbon dioxide ($etCO_2$) so that the computation unit 18 may generate a signal which is a function of the cardiac output.

The measurement sequence is as follows:

1. With valve 26 in the position illustrated in FIG. 2, $VCO_2$ and $etCO_2$ are recorded over three minutes. The volume of $VCO_2$ is calculated by integrating the instantaneous measurements of the capnometer sensor over the flow volume as indicated by sensor 40. The $etCO_2$ is calculated on a breath-by-breath basis using a peak detection algorithm which stores the maximum value of the transient $CO_2$ signal from the capnometer 16 for each breath. The inhaled air is not admixed to any appreciable degree with previously exhaled air.

2. The computation unit 18 then switches the valve 26 to the position illustrated in FIG. 3. The volume of the conduit 30 is then filled with exhaled breath, with the overflow being passed out through the bi-directional flow sensor 40. The volume of the passage 30 is preferably about 15–25% of the tidal volume of the subject. Typical tidal volumes range between 600 ml and 1000 ml and the volume of the chamber 30 is preferably about 150 ml. The subject therefore rebreathes carbon dioxide from the temporary dead space chamber for approximately thirty seconds. During this thirty second period breath-to-breath end-tidal carbon dioxide and total integrated volume of carbon dioxide are recorded.

3. The collected data are than processed by the computation unit 18 and the results are displayed or printed.

The unit can thus calculate and display the following parameters: oxygen consumption ($VO_2$), measured energy expenditure (MEE), carbon dioxide production ($VCO_2$, cardiac output (CO), respiratory exchange ratio (RER), minute ventilation (V), and end-tidal carbon dioxide ($etCO_2$).

The computation unit 18, in the cardiac output mode may employ a computation algorithm of the type described in the Capek and Roy paper.

Having thus described my invention I claim:

1. A respiratory gas analyzer for measuring the metabolic activity or cardiac output of a subject, comprising:

a respiratory connector operative to be supported in contact with a subject so as to pass inhaled and exhaled gasses as the subject breathes;

means for connecting to a source of respiratory gasses;

a bi-directional flow meter adapted to generate electrical signals as a function of the volume of gasses which pass through it in either direction;

a pass-through carbon dioxide scrubber operative to absorb carbon dioxide from gasses which pass through it;

a capnometer;

a valve shiftable between a first configuration and a second configuration;

conduits interconnecting said respiratory connector, said means for connecting to a source of respiratory gasses, said scrubber, said flow meter, said capnometer and said valve;

computer means for receiving the outputs of the flow meter and the capnometer;

means for controlling the position of the valve;

said computer being connected to said means for controlling the valving so as to interconnect the components in either a first configuration in which, upon inhalation by a subject substantially the entire inhaled volume is passed from the source of respiratory gasses, through the flow meter to the subject and upon exhalation by a subject substantially all of the exhaled gasses are passed through the flow meter in a direction opposite to the inhaled gasses, or a second configuration in which upon inhalation by a subject only a fraction of the inhaled gasses are passed through the flow meter from the source of respiratory gasses, with the balance constituting previously exhaled gasses stored in said conduits, and upon exhalation by a subject only a fraction of the exhaled gasses are passed through the flow meter in a direction opposite to the inhaled gasses, the balance being stored in said conduits, whereby the computer may calculate the cardiac output of a subject based on the difference between the carbon dioxide content of the exhaled gasses between the time the valve is in the first configuration and the time the valve is in the second configuration and the difference in the end-tidal carbon dioxide content of the exhaled breath between the times the valves are in the first configuration and the valves are in the second configuration; and means operative at such time as said valve is in said first configuration, whereby upon exhalation by a subject, the exhaled gasses are passed first through the scrubber, then through the flow meter in a direction opposite to the inhaled gasses, whereby the computer may generate a signal proportional to the integral of the difference between the inhaled and exhaled gas volumes over a period of time to calculate a subject's metabolic rate.

2. The metabolic gas analyzer of claim 1 wherein the scrubber may be connected to the conduits so that upon exhalation by a subject the exhaled gasses are passed first through the scrubber, then through the flow meter in a direction opposite to the inhaled gasses, or the scrubber may be removed from the conduit so that upon exhalation by a subject exhaled gasses passing through the flow meter in a direction opposite to the inhaled gasses are not first passed through the scrubber.

3. A respiratory gas analyzer useful for calculating the respiratory oxygen consumption per unit time or the cardiac output of a subject, comprising:

a respiratory connector operative to be supported in contact with the mouth of a subject so as to pass inhaled and exhaled gasses as the subject breathes;

means for connecting to a source of respiratory gasses;

a pass-through bi-directional flow meter adapted to generate electrical signals as a function of the volume of gasses which pass through it in either direction;

a pass-through carbon dioxide scrubber operative to absorb carbon dioxide from gasses which pass through it;

a capnometer;

a computer for receiving generated electrical signals from the flow meter and the capnometer;

conduits interconnecting said respiratory connector, said means for connecting to a source of respiratory gasses, said capnometer and said flow meter;

a connector for removably attaching the scrubber to the conduits; and valve means connected to the conduits for arranging the respiratory gas analyzer in either a first configuration in which, upon inhalation by a subject gasses are passed from the source of respiratory gasses through the flow meter to a subject so that substantially all of the inhaled gasses are passed through the flow meter or a second configuration wherein upon inhalation by a subject a portion of the inhaled gasses are derived from previously exhaled gas stored within the conduits and the balance is derived from the source of respiratory gasses through the flow meter, the computer being operative to calculate an electrical signal which is a function of the cardiac output of a subject based upon the difference in the carbon dioxide content in the expired gasses between the time that the valve is in the first configuration and the valve is in the second configuration, and the difference between the end-tidal carbon dioxide content of the exhaled breath between the times that the valve is in said first configuration and the time that the valve is in said second configuration; and means for connecting said scrubber to the conduits when said valve is in said first configuration, so that exhaled gasses are passed first through the scrubber, then through the flow meter in a direction opposite to the inhaled gasses, whereby the flow meter is operative to generate a signal proportional to the integral of the difference between the inhaled and exhaled gas volumes over a period of time to calculate the metabolic activity of a subject.

4. The respiratory gas analyzer of claim 3 in which the source of respiratory gasses is the atmosphere.

5. The respiratory gas analyzer of claim 3 in which said portion of inhaled gasses which are derived from the previously exhaled gasses represents about 10–60% of the entire inhaled gas.

* * * * *